United States Patent
Veech et al.

(10) Patent No.: US 11,230,722 B2
(45) Date of Patent: Jan. 25, 2022

(54) NUTRITIONAL SUPPLEMENTS AND THERAPEUTIC COMPOSITIONS COMPRISING (R)-3-HYDROXYBUTYRATE DERIVATIVES

(71) Applicants: Oxford University Innovation Limited, Oxford (GB); U.S. DEPT. OF HEALTH AND HUMAN SERVICES (DHHS), U.S. GOVERNMENT, Bethesda, MD (US)

(72) Inventors: Richard Lewis Veech, Rockville, MD (US); Michael Todd King, Gaithersburg, MD (US); Kieran Clarke, Oxford (GB)

(73) Assignees: Oxford University Innovation Limited, Oxford (GB); U.S. Dept. Of Health and Human Services, (DHHS), U.S. Government, Bethesda, MD (US)

(*) Notice: Subject to any disclaimer, the term of this patent is extended or adjusted under 35 U.S.C. 154(b) by 0 days.

(21) Appl. No.: 15/914,676

(22) Filed: Mar. 7, 2018

(65) Prior Publication Data

US 2018/0195096 A1    Jul. 12, 2018

Related U.S. Application Data

(63) Continuation of application No. 10/559,258, filed as application No. PCT/US2004/018016 on Jun. 3, 2004, now abandoned.

(60) Provisional application No. 60/529,873, filed on Dec. 15, 2003, provisional application No. 60/475,848, filed on Jun. 3, 2003.

(51) Int. Cl.
| | |
|---|---|
| *C12P 7/26* | (2006.01) |
| *C12P 7/62* | (2006.01) |
| *C07C 69/675* | (2006.01) |
| *C07C 59/01* | (2006.01) |
| *C07C 51/09* | (2006.01) |
| *C08G 63/06* | (2006.01) |
| *C07H 13/04* | (2006.01) |

(52) U.S. Cl.
CPC ............. *C12P 7/625* (2013.01); *C07C 51/09* (2013.01); *C07C 69/675* (2013.01); *C07H 13/04* (2013.01); *C08G 63/06* (2013.01); *C12P 7/26* (2013.01); *C12P 7/62* (2013.01); *Y02P 20/54* (2015.11)

(58) Field of Classification Search
CPC ....... C07C 51/09; C07C 69/675; C07H 13/04; C12P 7/26; C12P 7/625; C08G 63/06
USPC ................ 424/78.37; 514/25; 525/54.2, 437; 536/119
See application file for complete search history.

(56) References Cited

U.S. PATENT DOCUMENTS

| | | | |
|---|---|---|---|
| 3,984,566 A | 10/1976 | Van Scott et al. | |
| 4,380,549 A | 4/1983 | Van Scott et al. | |
| 5,112,865 A | 5/1992 | Nichels et al. | |
| 5,281,691 A | 1/1994 | Hubbs et al. | |
| 5,468,507 A | 11/1995 | Czap | |
| 5,654,266 A | 8/1997 | Chen et al. | |
| 5,665,831 A | 9/1997 | Neuenschwander et al. | |
| 5,693,850 A | 12/1997 | Birkhahn et al. | |
| 6,126,953 A | 10/2000 | Costa et al. | |
| 6,136,862 A * | 10/2000 | Hiraide ................ | A61K 31/19 514/546 |
| 6,207,856 B1 | 3/2001 | Veech | |
| 6,268,167 B1 | 7/2001 | Wild et al. | |
| 6,316,038 B1 | 11/2001 | Veech | |
| 6,323,237 B1 | 11/2001 | Veech | |
| 6,380,244 B2 | 4/2002 | Martin et al. | |
| 6,544,960 B1 | 4/2003 | Eldred et al. | |
| 6,939,570 B1 | 9/2005 | Snow et al. | |
| 7,351,736 B2 | 4/2008 | Veech | |
| 7,947,736 B2 | 5/2011 | Gross | |
| 8,101,653 B2 | 1/2012 | Veech | |
| 8,642,654 B2 | 2/2014 | Clarke | |
| 9,034,613 B2 | 5/2015 | Robertson et al. | |
| 9,211,275 B2 | 12/2015 | Clarke et al. | |
| 9,579,302 B2 | 2/2017 | Veech et al. | |
| 2001/0014696 A1 | 8/2001 | Veech et al. | |

(Continued)

FOREIGN PATENT DOCUMENTS

| | | |
|---|---|---|
| CA | 1330307 C | 6/1994 |
| CA | 2173270 A | 10/1996 |

(Continued)

OTHER PUBLICATIONS

Abdelwahab et al. (2012) "The Ketogenic Diet Is an Effective Adjuvant to Radiation Therapy for the Treatment of Malignant Glioma," PLOS ONE. 7(5):E36197. pp. 1-7.

(Continued)

*Primary Examiner* — Ganapathy Krishnan
(74) *Attorney, Agent, or Firm* — Lathrop GPM LLP; Brian C. Trinque

(57) ABSTRACT

Novel compounds and compositions containing (R)-3-hydroxybutyrate derivatives are disclosed. The compounds and compositions can be used as nutritional supplements to increase physical performance and as therapeutics to ameliorate symptoms of medical conditions, particularly neurological conditions, such as Alzheimer's and similar conditions. Novel methods for making R-3-hydroxybutyrate derivatives also are disclosed. Exemplary methods employ a supercritical solvent, such as supercritical carbon dioxide, and employ a lipase catalyzed esterification or transesterification reaction to produce the (R)-3-hydroxybutyrate derivatives.

6 Claims, 1 Drawing Sheet

(56) References Cited

U.S. PATENT DOCUMENTS

| | | | |
|---|---|---|---|
| 2001/0041741 A1 | 11/2001 | Sole et al. |
| 2001/0047008 A1 | 11/2001 | Baraldi |
| 2002/0006959 A1 | 1/2002 | Henderson |
| 2002/0013339 A1 | 1/2002 | Martin et al. |
| 2002/0035231 A1 | 3/2002 | Whitehouse et al. |
| 2003/0022937 A1 | 1/2003 | Veech et al. |
| 2004/0006263 A1 | 1/2004 | Anderson et al. |
| 2004/0063661 A1 | 4/2004 | Linnane |
| 2004/0171671 A1 | 9/2004 | Veech |
| 2004/0266872 A1 | 12/2004 | Veech et al. |
| 2005/0129783 A1 | 6/2005 | McCleary et al. |
| 2005/0165318 A1 | 7/2005 | Brodnick et al. |
| 2005/0181275 A1 | 8/2005 | Jang |
| 2005/0182235 A1 | 8/2005 | Zhong et al. |
| 2006/0078596 A1 | 4/2006 | Clarke et al. |
| 2006/0280721 A1 | 12/2006 | Veech et al. |
| 2007/0179197 A1 | 8/2007 | Henderson et al. |
| 2008/0287372 A1 | 11/2008 | Henderson et al. |
| 2009/0197952 A1 | 8/2009 | Hashim et al. |
| 2009/0253781 A1 | 10/2009 | Veech |
| 2010/0298294 A1 | 11/2010 | Clarke et al. |
| 2011/0237666 A1 | 9/2011 | Clarke et al. |
| 2012/0064611 A1 | 3/2012 | Robertson et al. |
| 2012/0071548 A1 | 3/2012 | Veech |
| 2012/0213835 A1 | 8/2012 | Neas et al. |
| 2013/0102663 A1 | 4/2013 | Clarke et al. |
| 2014/0194509 A1 | 7/2014 | Clarke et al. |
| 2014/0308719 A1 | 10/2014 | Clarke et al. |
| 2015/0065571 A1 | 3/2015 | Clarke et al. |
| 2015/0164855 A1 | 6/2015 | Clarke et al. |
| 2015/0250755 A1 | 9/2015 | Veech et al. |
| 2016/0030314 A1 | 2/2016 | Clarke et al. |
| 2016/0193173 A1 | 7/2016 | Clarke et al. |
| 2017/0196827 A1 | 7/2017 | Veech et al. |

FOREIGN PATENT DOCUMENTS

| | | | |
|---|---|---|---|
| CN | 1483355 A | 9/2002 | |
| CN | 1552315 A | 12/2004 | |
| DE | 20205184 U | 12/2002 | |
| EP | 0 266 217 A2 | 5/1988 | |
| EP | 0 537 113 A1 | 4/1993 | |
| EP | 0 552 896 A1 | 7/1993 | |
| EP | 0 721 740 A1 | 7/1996 | |
| EP | 1 568 780 A1 | 8/2005 | |
| EP | 1 809 235 B1 | 7/2007 | |
| EP | 2 875 812 A1 | 5/2015 | |
| GB | 1524611 A | 9/1978 | |
| GB | 0312603.4 | 6/2003 | |
| GB | 0313760.1 | 6/2003 | |
| GB | 2511941 A | 9/2014 | |
| JP | S54-138126 A | 10/1979 | |
| JP | S57-047446 A | 3/1982 | |
| JP | S63-112998 A | 5/1988 | |
| JP | H01-095730 A | 4/1989 | |
| JP | H01-160917 A | 6/1989 | |
| JP | H03-083950 A | 4/1991 | |
| JP | H04-112825 A | 4/1992 | |
| JP | H07-076513 A | 3/1995 | |
| JP | H08-191664 A | 7/1996 | |
| JP | H10-175855 A | 6/1998 | |
| JP | H10-265378 A | 10/1998 | |
| JP | H10-313819 A | 12/1998 | |
| JP | 2001-515510 A | 9/2001 | |
| JP | 2005-247821 A | 9/2005 | |
| JP | 2008-513017 A | 5/2008 | |
| JP | 2008-127369 A | 6/2008 | |
| JP | 2008-263825 A | 11/2008 | |
| JP | 2009-532496 A | 9/2009 | |
| JP | 2012-500264 A | 1/2012 | |
| JP | 2016-512207 A | 4/2016 | |
| SU | 507322 A | 3/1976 | |
| WO | 1987/003806 A1 | 7/1987 | |
| WO | 1995/009144 A1 | 4/1995 | |
| WO | 1998/041200 A1 | 9/1998 | |
| WO | 1998/041201 A1 | 9/1998 | |
| WO | WO 98/41200 * | 9/1998 | ............ A61K 31/19 |
| WO | 1999/024451 A2 | 5/1999 | |
| WO | 2000/004895 A1 | 2/2000 | |
| WO | 2000/015216 A1 | 3/2000 | |
| WO | 2001/013877 A1 | 3/2001 | |
| WO | 2001/051645 A1 | 7/2001 | |
| WO | 2002/006368 A2 | 1/2002 | |
| WO | 2003/012417 A2 | 2/2003 | |
| WO | 2003/056319 A2 | 7/2003 | |
| WO | 2003/097860 A1 | 11/2003 | |
| WO | 2004/105742 A1 | 12/2004 | |
| WO | 2004/108740 A1 | 12/2004 | |
| WO | 2006/020137 A2 | 2/2006 | |
| WO | 2006/031941 A2 | 3/2006 | |
| WO | 2006/061624 A1 | 6/2006 | |
| WO | 2006/070337 A2 | 7/2006 | |
| WO | 2007/001883 A2 | 1/2007 | |
| WO | 2007/063037 A2 | 6/2007 | |
| WO | 2007/115282 A2 | 10/2007 | |
| WO | 2007/115934 A1 | 10/2007 | |
| WO | 2008/074473 A2 | 6/2008 | |
| WO | 2008/119032 A1 | 10/2008 | |
| WO | 2008/140828 A1 | 11/2008 | |
| WO | 2009/023357 A2 | 2/2009 | |
| WO | 2009/045481 A1 | 4/2009 | |
| WO | 2009/089144 A1 | 7/2009 | |
| WO | 2010/021766 A1 | 2/2010 | |
| WO | 2010/120300 A1 | 10/2010 | |
| WO | 2011/101171 A1 | 8/2011 | |
| WO | 2011/121540 A1 | 10/2011 | |
| WO | 2012/113415 A1 | 8/2012 | |
| WO | 2013/150153 A1 | 10/2013 | |
| WO | 2014/071389 A1 | 5/2014 | |
| WO | 2014/139599 A1 | 9/2014 | |
| WO | 2014/153416 A1 | 9/2014 | |

OTHER PUBLICATIONS

Baron et al. (1991) "Mechanism of insulin resistance in insulin-dependent diabetes mellitus: a major role for reduced skeletal muscle blood flow," J. Clin. Endocrinol. Metab. 73(3):637-643.

Boehm et al. (2001) "Increased uncoupling proteins and decreased efficiency in the palmitate-perfused hyperthyroid rat heart," Am. J. Physiol. Heart Circ. Physiol. 2809(3):H977-H983.

Boyarinov et al. (1984) "Effect of Sodium hydroxybutyrate on myocardial high-energy phosphates, function, and ultrastructure after blood loss," Byulleten Eksperimental'noi Biologii i Meditsiny. 97(3):289-292.

Buteau (2009) "Obviousness of Enantiomers over Prior Art Racemates," The Journal of High Technology Law. L22. pp. 42-49.

Casey et al. (1990) In; Advanced Practical Organic Chemistry. Blackie. Glasgow and London, U.K. pp. 158-160.

Chatham et al. (1999) "Preferential inhibition of lactate oxidation relative to glucose oxidation in the rat heart following diabetes," Cardiovasc Res. 43(1):96-106.

Chatham et al. (2002) "Cardiac carbohydrate metabolism in Zucker diabetic fatty rats," Cardiovasc Res. 55(1):104-112.

Chen et al. (Feb. 2016) "Beta-hydroxybutyrate reduces alcoholic steatohepatits (ASH) via activation of the GPR 109A Receptor," Proceedings of the American Society for Hematology, 2016. Abstract No. 26. pp. 143 144.

Chen et al. (Nov. 13, 2016) "β-hydroxybutyrate protects from alcoholic hepatitis via a GPR109a-C/EBPβ dependent pathway," AASLD LiverLearning. Abstract No. 1629. Accessible on the Internet at URL: http://liverlearning.aasld.org/aasld/2016/thelivermeeting/144521/yonglin.chen.b-hydroxybutyrate.protects.from.alcoholic.hepatitis.via.a.html. [Last Accessed Apr. 5, 2017].

Clark et al. (2005) "Dilated Cardiomyopathy and Acute Liver Injury Associated with Combined Use of Ephedra, Hydroxybutyrate, and Anabolic Steroids" Pharmacotherapy 25(5):756-761.

Cole et al. (2011) "A high fat diet increases mitochondrial fatty acid oxidation and uncoupling to decrease efficiency in rat heart," Basic Res. Cardiol 106:447-457.

(56) References Cited

OTHER PUBLICATIONS

Cox et al. (Oct. 29, 2014) "Acute nutritional ketosis: implications for exercise performance and metabolism," Extrem. Physiol Med 3:17. pp. 1-9.
Davey et al. (1988) "Radioprotection of rat subependymal plate with 4-0H sodium butyrate," NCI Monogr. (6):231-234.
Demir et al. (2001) "Serum HbA1c levels and exercise capacity in diabetic patients," Jpn. Heart J. 42(5):607-616.
Desrochers et al. (1992) "Metabolism of R and S-1,3-butanediol in perfused livers from meal-fed and starved rats," Biochem. J 285:647-653.
Desrochers et al. (1995) "Metabolism of (R,S)-1,3-butanediol acetoacetate esters, potential parenteral and enteral nutrients in conscious pigs," Am. J. Physiol. 268:E660-667.
Desrochers et al. (1995) "R, S-1, 3-butanediol acetoacetate esters, potential alternates to lipid emulsions for total parenteral nutrition," Journal of Nutritional Biochemistry 6(2): 111-118.
Eagles et al. (1997) "The effects of combined treatment with Beta-1-selective receptor antagonists and lipid-lowering drugs on fat metabolism and measures of fatigue during moderate intensity exercise: a placebo-controlled study in healthy subjects," Brit. J. Clinical Pharmacol. 43:291-300.
Edegger et al. (2006) "Regia- and Stereoselective Reduction of Diketones and Oxidation of Dials by Biocatalytic Hydrogen Transfer," Eur. J. Org. Chem. 2006(8):1904-1909.
Estacio et al. (1998) "The association between diabetic complications and exercise capacity in NIDDM patients," Diabetes Care. 21(2):291-295.
Farmer et al. (1973) "Radioprotective Thiazolidines from beta-keto esters," J. Med. Chem. 16(4):411-413.
Felig et al. (1971) "Amino acid metabolism in exercising man." J. Clin. Invest. 50(12):2703-2714.
Frayn (2003) In; Metabolic Regulation: A Human Perspective. 2nd Ed. Blackwell Science, pp. 94-96.
Gangemi "Enhancing Athletic Performance by Predicting Fatigue and Preventing Muscle Failure," Accessible on the Internet at URL: http://www.drgangemi.com/wp-content/uploads/2011/01/GANGEMI-PREDICTING-FATIGUE-AND-MUSCLE-FAILURE.pdf. [Last Accessed Sep. 20, 2011].
Goldbort et al. (1976) "Butanediols: Selection, open field activity, and NAD reduction by liver extracts in inbred mouse strains," Pharmacology Biochemistry and Behaviour. 5(3):263-268.
Ozzo et al. (2002) "Mismatch between insulin-mediated glucose uptake and blood flow in the heart of patients with Type II diabetes," Diabetologia. 45(10):1404-1409.
Kalaitzakis et al. (2005) "Highly Stereoselective Reductions of a-Aikyl-1,3-diketones and a-Aikyi-Jl-keto Esters Catalyzed by Isolated NADPH-Dependent Ketoreductases," Org. Lett. 7(22):4799-4801.
Kashiwaya et al. (2013) "A ketone ester diet exhibits anxiolytic and cognition-sparing properties, and lessens amyloid and tau pathologies in a mouse model of Alzheimer's disease," Neurobiology of Aging. 34(6): 1530-1539.
Kemper et al. (Oct. 26, 2015) "An Ester of β-Hydroxybutyrate Regulates Cholesterol Biosynthesis in Rats and a Cholesterol Biomarker in Human," Lipids 50(12):1185-1193.
Knowler et al. (2002) "Reduction in the incidence of type 2 diabetes with lifestyle intervention or metformin," New Engl. J Med 346:393-403.
Kohut et al. (1995) "Effects of decreased free fatty acids on fatigue during exercise with carbohydrate feedings," Medicine and Science in Sports & Exercise. 27(5 Suppl):S102.
Komiyama et al. (2000) "Near-infrared spectroscopy grades the severity of intermittent claudication in diabetes more accurately than ankle pressure measurement," British Journal of Surgery. 87(4):459-466.
Komiyama et al. (2004) "Effects of a 4-week 70% high carbohydrate / 15% low fat diet on glucose tolerance and on lipid profiles," Diabetes Res Clin. Pract. 64(1):11-18.
Kulinskii et al. (1993) "The radioprotective effect of GABA-tropic substances, gamma-hydroxybutyrate and piracetam," Radiobiologiia. 33(1):133-136.—English Abstract Only.
Kwiterovich et al. (2003) "Effect of a high-fat ketogenic diet on plasma levels of lipids, lipoproteins, and apolipoproteins in children," JAMA. 290(7):912-920.
Lanni et al. (2002) "De Novo Expression of Uncoupling Protein 3 is Associated to Enhanced Mitochondrial Thioesterase-1 Expression and Fatty Acid Metabolism in Liver of Fenofibrate-treated Rats," FEBS Letters. 525:7-12.
Larios et al. (2004) "Synthesis of flavor and fragrance esters using Candida antarctica lipase," Appl. Microbiol. Biotechnol. 65:373-376.
Libby et al. (2002) "Diabetic macrovascular disease. The glucose paradox?" Circulation. 106(22):2760-2763.
Lodi et al. (1999) "Reduced cytosolic acidification during exercise suggests defective glycolytic activity in skeletal muscle of patients with Becker muscular dystrophy. An in vivo 31P magnetic resonance spectroscopy study," Brain. 121(1):121-130.
Madsen et al. (1999) "Near-infrared oximetry of the brain," Prog. Neurobiol. 58(6):541-560.
Mahler et al. (1999) "Type 2 diabetes mellitus: update on diagnosis, pathophysiology, and treatment," J. Clin. Endocrinol. Metab. 84(4):1165-1171.
Mahley et al. (2006) "Drug Therapy of Dyslipidemia," In; Goodman & Gilman's the Pharmacological Basis of Therapeutics. 11th Ed. Eds.: Brunton et al. McGraw-Hill. New York, New York. pp. 948-953.
Meyer et al. (1997) "Myocardial blood flow and glucose metabolism in diabetes mellitus," Am. J. Cardiol. 80(3,Suppl 1):94A-101A.
Mori et al. (1984) "Synthesis of the Propionates of (2R, 8R)- and (2S, 8R)-8-methyl-2-decanol, the pheromone of the Western corn rootworm, employing chiral compounds of microbial origin as starting material," Tetrahedron. 40(2):299-303.
Mori et al. (1987) "New synthesis of both enantiomers of grandisol, the boll weevil pheromon," Tetrahedron. 43(10):2229-2239.
Murray et al. (2004) "Uncoupling Proteins in Human Heart," Lancet. 364:1786-1788.
Murray et al. (2005) "Plasma Free Fatty Acids and Peroxisome Proliferator-Activated Receptor a in the Control of Myocardial Uncoupling Protein Levels," Diabetes. 54(12):3496-3502.
Nair et al. (1988) "Effect of beta-hydroxybutyrate on whole-body leucine kinetics and fractional mixed skeletal muscle protein synthesis in humans," J. Clin. Invest. 82(1):198-205.
Meubauer et al. (1997) "Myocardial Phosphocreatine-to-ATP Ratio is a predictor of mortality in patients with dilated cardiomyopathy," Circulation. 96:2190-2196.
Supplementary European Search Report and Written Opinion corresponding to European Patent Application No. 09701051.6, dated Jan. 19, 2011.
Clarke et al. (2012) "Oral 28-day and developmental toxicity studies of (R)-3-hydroxybutyl (R)-3-hydroxybutyrate," Regulatory Toxicology & Pharmacology. 63(2):196-208.
Laffel (1999) "Ketone bodies: a review of physiology, pathophysiology and application of monitoring to diabetes," Diabetes Metabol. Res. Rev. 15(6):412-426.
Leckey et al. (Oct. 2017) "Ketone Diester Ingestion Impairs Time-Trial Performance in Professional Cyclists," Front Physiol. 8:806.
Ley (2008) "Masking Bitter Taste by Molecules," Chem. Percept. 1:58-77.
Lunde et al. (1998) "Skeletal muscle fatigue in normal subjects and heart failure patients. Is there a common mechanism?" Acta Physiol. Scand 162:215-228.
Ojeda et al. (1977) "[Radiation response of mitochondria in dependence on their metabolic status (author's transl)]," Strahlentherapie. 153(2): 117-123.
Suzuki et al. (1986) "Acetylputrescine deacetylase from Micrococcus luteus K-11," Biochimica et Biophysica Acta. 882:140-142.
Westerblad et al. (2002) "Recent advances in the understanding of skeletal muscle fatigue," Curr. Opin. Rheumatol. 14:648-652.
Wilson (1996) "Evaluation of Skeletal Muscle Fatigue in Patients with Heart Failure," J. Mol. Cell/ Cardiol. 28:2287-2292.

(56) References Cited

OTHER PUBLICATIONS

Newsholme et al. (1986) In; Biochemistry for the Medical Sciences. John Wiley & Sons Chichester, U.K. pp. 324-331.
O'Neill et al. (1994) "A simple enantioselective synthesis of γ-valerolactone," Tetrahedron Asymmetry. 5(1):117-118.
Ostrovskaya et al. (1981) "Effect of prolonged administration of sodium hydroxybutyrate on the working capacity and muscle tissue in rats," Farmakologiya I Toksikologiya. 44(5):534-539.—Only English Abstract Provided.
Paolisso et al. (1999) "Prognostic importance of insulin-mediated glucose uptake in aged patients with congestive heart failure secondary to mitral and/or aortic valve disease," Am. J. Cardiol. 83(9):1338-1344.
Perez-Jimenez et al. (2001) "A Mediterranean and a high-carbohydrate diet improve glucose metabolism in healthy young persons," Diabetologia. 44(11)12038-2043.
Puchowicz et al. (2000) "Dog model of therapeutic ketosis induced by oral administration of R,S-1,3-butanediol diacetoacetate," J. Nutr. Biochem. 11:281-287.
Richieri et al. (1995) "Unbound free fatty acid levels in human serum," Journal of Lipid Research. 36(2):229-240.
Rodrigues et al. (1998) "Metabolic disturbances in diabetic cardiomyopathy," Molecular and Cellular Biochemistry. 180(1-2)153-57.
Rossi et al. (2000) "Suppression of feed intake after parenteral administration of D-beta-hydroxybutyrate in pygmy goats," J. Vet. Med. A. 47:9-16.
Salehizadeh et al. (2004) "Production of polyhydroxyalkanoates by mixed culture: recent trends and biotechnological importance," Biotechnol. Advances. 22:261-279.
Sato et al. (1995) "Insulin, ketone bodies, and mitochondrial energy transduction," FASEB J. 9(8):651-658.
Scheuermann-Freestone et al. (2003) "Abnormal cardiac and skeletal muscle energy metabolism in patients with type 2 diabetes," Circulation. 107(24):3040-3046.
Seebach et al. (1993) "Direct Degradation of the Biopolymer Poly[(R)-3-Hydroxybutyric Acid] to (R)-3-Hydroxybutanoic Acid and its Methyl Ester," Organic Syntheses, Coll. vol. 9., p. 483 (1998); vol. 71., p. 39.
Shaw et al. (1984) "Influence of beta-hydroxybutyrate infusion on glucose and free fatty acid metabolism in docs," Am. J. Phys. 247:E756-764.
Sherwin et al. (1975) "Effect of ketone infusions on amino acid and nitrogen metabolism in man" J. Clin. Invest. 55(6) 1382-1390.
Sidell et al. (2002) "Thiazolidinedione treatment normalizes insulin resistance and ischemic injury in the Zucker fatty rat heart," Diabetes. 51(4):1110-1117.
Silva et al. (2004) "Poly-3-hydroxybutyrate (P3HB) production by bacteria from xylose, glucose and sugarcane bagasse hydrolysate," J. Ind. Microbiol. Biotechnol. 31:245-254.
Simons et al. ( 1982) "Long term treatment with Slow Release Oxprenolol Alone, or in Combination with other Drugs Effects on Blood Pressure, Lipoproteins and Exercise Performance," Aust N. Z. J. Med. 12:612-616.
Smith et al. (1975) "Initial effect of injury on ketone bodies and other blood metabolites," Lancet. 1:7897. pp. 1-3.
Smith et al. (2002) "Magnetic Resonance Spectroscopy in Medicine: Clinical Impact," Progress in Nuclear Magnetic Resonance Spectroscopy. 40:1-34.
Stanley et al. (1997) "Regulation of energy substrate metabolism in the diabetic heart," Cardiovasc. Res. 34(1):25-33.
Taegtmeyer et al. (2002) "Adaptation and maladaptation of the heart in diabetes: Part I. General concepts," Circulation. 105(14):1727-1733.
Tinnikov et al. (1999) "Colorimetric micro-determination of free fatty acids in plasma using microplate readers," Clinica Chemica Acta. 281(1-2):159-162.
Tobin et al. (1972) "Effect of 1,3-Butanediol and Propionic Acid on Blood Ketones, lipids d Metal Ions in Rats", Journal of Nutrition. 102(8):1001-1008.

Toubro et al. (1998) "Twenty-four-hour respiratory quotient: the role of diet and familial resemblance," J. Clin. Endocrinol. Metabol. 83(8):2758-2764.
Tunaru et al. (2003) "PUMA-G and HM74 are receptors for nicotinic acid and mediate its anti-lipolytic effect," Nat. Med. 9(3):352-355.
Turner et al. "Glycemic control with diet, sulfonylurea, metformin, or insulin in patients with type 2 diabetes mellitus: progressive requirement for multiple therapies (UKPDS 49)." Jama 281.21 (1999): 2005-2012.
Wu et al. (1987) "Ketone bodies inhibit leucine degradationin chick skeletal muscle," International J. of Biochem. 19(10):937-943.
Zange et al. (2002) "Creatine Supplementation Results in Elevated Phosphocreatine/Adenosine Triphosphate (ATP) Ratios in the Calf Muscle of Athletes but Not in Patients with Myopathies," Annals of Neurology. 53(1):126-127.
Zhu et al. (2006) "A recombinant ketoreductase tool-box. Assessing the substrate selectivity and stereoselectivity toward the reduction of JI-ketoesters," Tetrahedron 62:901-905.
Examination Report corresponding to Great Britain Patent Application No. 1404400.2, dated Aug. 18, 2014.
International Preliminary Report on Patentability corresponding to International Patent Application No. PCT/US2009/030095 dated Jul. 6, 2010.
International Preliminary Report on Patentability corresponding to International Patent Application No. PCT/US2009/040773, dated Oct. 18, 2011.
International Search Report with Written Opinion corresponding to International Patent Application No. PCT/EP2011/000833, dated Jun. 22, 2011.
International Search Report with Written Opinion corresponding to International Patent Application No. PCT/EP2013/057250, dated Jun. 11, 2013.
International Search Report with Written Opinion corresponding to International Patent Application No. PCT/EP2013/069189, dated Aug. 12, 2014.
International Search Report with Written Opinion corresponding to International Patent Application No. PCT/EP2014/055158, dated Jun. 25, 2014.
International Search Report with Written Opinion corresponding to International Patent Application No. PCT/EP2014/067027, dated Oct. 30, 2014.
International Search Report with Written Opinion corresponding to International Patent Application No. PCT/3B2004/002286, dated Oct. 11, 2004.
International Search Report with Written Opinion corresponding to International Patent Application No. PCT/JS2004/018016, dated Apr. 15, 2005.
International Search Report with Written Opinion corresponding to International Patent Application No. PCT/US2009/030095, dated Feb. 23, 2009.
International Search Report with Written Opinion corresponding to International Patent Application No. PCT/US2009/040766, dated Aug. 6, 2009.
International Search Report with Written Opinion corresponding to International Patent Application No. PCT/US2009/040773, dated Feb. 22, 2010.
International Search Report with Written Opinion corresponding to International Patent Application No. PCT/US2013/068545, dated Jan. 20, 2014.
Search and Examination Report corresponding to Great Britain Patent Application No. 1404400.2, dated Mar. 26, 2014.
Search and Examination Report corresponding to Great Britain Patent Application No. 1404577.7, dated Oct. 23, 2014.
Search and Examination Report corresponding to Great Britain Patent Application No. 1414016.4, dated Aug. 29, 2014.
Search Report corresponding to Great Britain Patent Application No. 1002983.3, dated Jun. 10, 2010.
Search Report corresponding to Great Britain Patent Application No. 1304467.2, dated Aug. 23, 2013.

(56) References Cited

OTHER PUBLICATIONS

Search Report corresponding to Great Britain Patent Application No. 1314127.0. dated Jan. 31, 2014.

\* cited by examiner

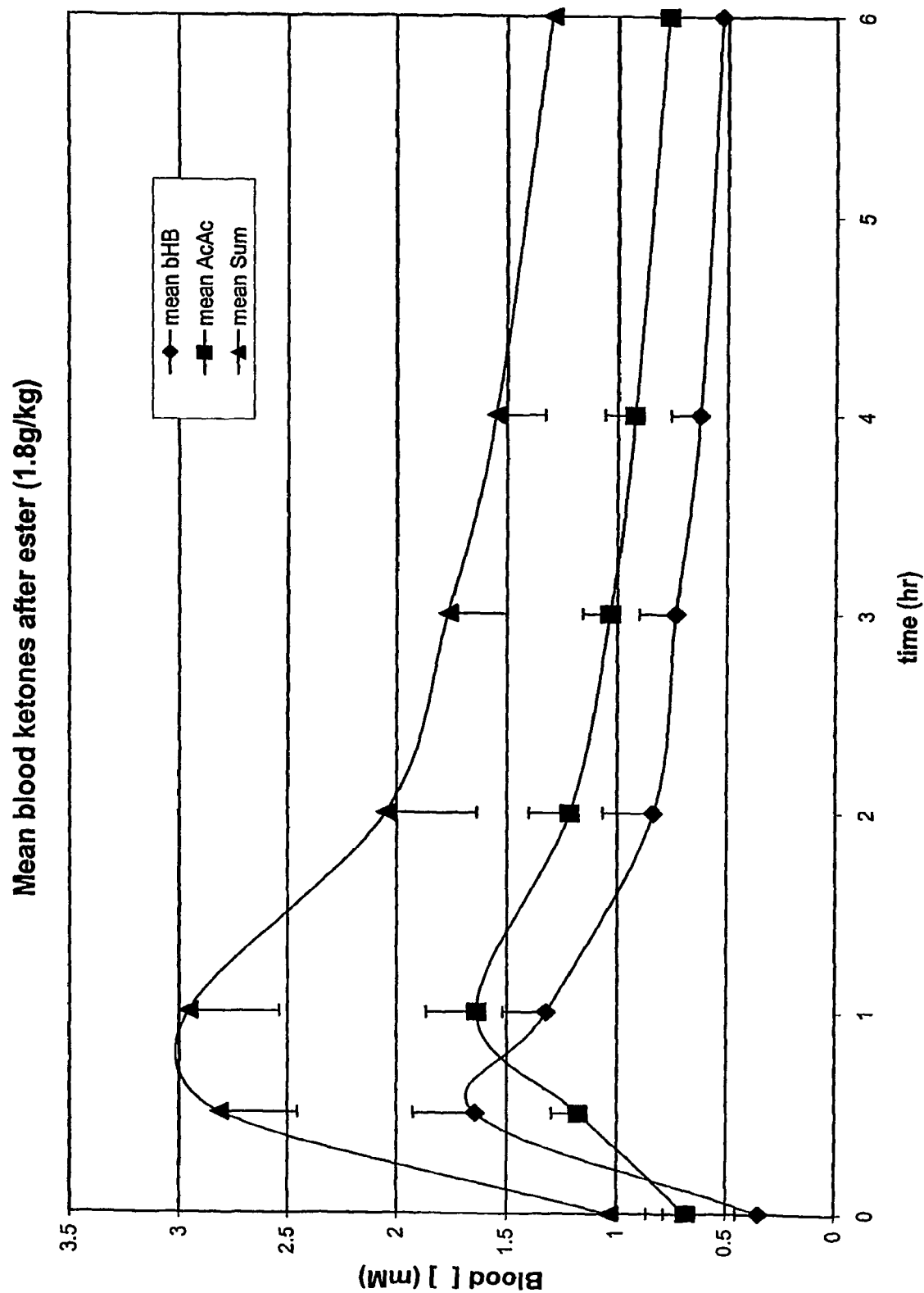

NUTRITIONAL SUPPLEMENTS AND THERAPEUTIC COMPOSITIONS COMPRISING (R)-3-HYDROXYBUTYRATE DERIVATIVES

CROSS REFERENCE TO RELATED APPLICATIONS

This application is a continuation of U.S. application Ser. No. 10/559,258, filed on Jun. 8, 2006, which is a 35 U.S.C. § 371 filing of International Application PCT/US2004/018016, filed Jun. 3, 2004, which claims the benefit of U.S. Provisional Application Nos. 60/475,848 and 60/529,873, filed Jun. 3, 2003 and Dec. 15, 2003, respectively. These prior applications are incorporated herein by reference in their entireties.

FIELD

The disclosure concerns compounds and compositions containing (R)-3-hydroxybutyrate derivatives effective for elevating blood concentrations of ketone bodies and methods for using such compounds and compositions as nutritional supplements or for treating medical conditions.

BACKGROUND

During periods of carbohydrate deprivation, the body utilizes energy obtained from the metabolism of fats. During fat metabolism, fats are converted to acetoacetate and 3-hydroxybutyric acid, which are known as ketone bodies, and large quantities of these substances accumulate in the blood. This condition, which is known as ketosis, commonly occurs during starvation. When blood ketone body concentrations are elevated to levels found in prolonged starvation, they provide the major source of energy for the brain.

Mild ketosis, in which ketone bodies are used by the body as an energy source, has been demonstrated to have therapeutic effects in several disease states. For example, refractory epilepsy was initially treated with success by prolonged fasting. In view of this result, Russell Wilder, of the Mayo Clinic, proposed a high fat, low carbohydrate diet, termed a "ketogenic diet," for inducing ketosis and achieving the beneficial effects of starvation for treating epilepsy. The ketogenic diet generally includes four parts fat to one part protein with minimal carbohydrate intake.

The success of the ketogenic diet in treating epilepsy derives from the brain's ability to metabolize ketone bodies. During prolonged fasting, free fatty acids are converted in the liver to (R)-3-hydroxybutyrate and acetoacetate to provide energy for the brain while preserving muscle mass from conversion into glucose. Under such fasting conditions, total blood ketone concentration typically is maintained at from about 5 to about 7 mM. Unfortunately, the ability of the brain to use ketone bodies has not been exploited therapeutically beyond the use of the ketogenic diet to treat epilepsy. The ketogenic diet has many drawbacks, some of which include the elevated triglyceride levels, cholesterol levels, or both caused by the high fat diet. Moreover, the 4 to 1 ratio of fat to protein is unpalatable for many subjects.

Induction of mild ketosis has been suggested as a possible treatment for several diseases. For example, mild ketosis mimics the acute effects of insulin, and thus may be useful for treating diabetics, particularly insulin resistant type I diabetics (Kashiwaya et al. *Am. J. Cardiol.* 1997, 80, 50A-64A).

Moreover, because the metabolism of ketone bodies results in a 28% increase in the hydraulic work produced by a ketone body-perfused heart per unit of oxygen relative to a glucose-perfused heart, it has been suggested that induction of ketosis could provide some cardiovascular benefit under conditions of hypoxia (Veech, R. L. The Therapeutic Implications of Ketone Bodies. *Prostaglandins, Leukotrienes and Essential Fatty Acids*, In press).

Treatment of human tissues with (R)-3-hydroxybutyrate results in several beneficial therapeutic and nutritional effects. For example, cardiac efficiency and brain metabolic efficiency are increased and the effects of neurodegenerative disorders, such as Alzheimer's and Parkinson's diseases are reduced. Moreover, (R)-3-hydroxybutyrate can serve as an alternative physiologic energy source. Indeed, Cahill and coworkers established that greater than 60% of the metabolic energy needs of the brain can be supplied by ketone bodies as a substitute for glucose. (Owen et al. *J. Clin. Invest.* 1967, 46, 1589-1595).

In addition to being a unique, high energy metabolic substrate, (R)-3-hydroxybutyrate has potential therapeutic applications including treatment of Alzheimer's disease and Parkinson's disease. These potential uses have not yet been realized because a suitable form for administering (R)-3-hydroxybutyrate or a metabolic precursor thereof has not been developed.

In theory, (R)-3-hydroxybutyrate and acetoacetate could be administered directly to achieve elevated levels of ketone bodies in a subject. However, direct administration of these compounds is impractical and dangerous. For example, direct administration of either (R)-3-hydroxybutyrate or acetoacetate in their acid form can result in significant acidosis following rapid absorption from the gastrointestinal tract. Administration of the sodium salt of these compounds is also unsuitable due to a potentially dangerous sodium overload that would accompany administration of therapeutically relevant amounts of these compounds (Desrochers et al. *J. Nutr. Biochem.* 1995, 6, 111-118). To circumvent these problems, researchers have attempted to administer (R)-3-hydroxybutyrate oligomers, thereby reducing the ratio of salt to (R)-3-hydroxybutyrate equivalents (U.S. Pat. No. 6,136,862 to Hiraide et al).

Prior (R)-3-hydroxybutyrate derivatives for biological use generally contain mixtures of different products. For example, published U.S. patent application Ser. No. 09/359,086 of Martin et al. (Publication No. 20020013339, hereinafter "the '339 publication") describes mixtures of (R)-3-hydroxybutyrate oligomers defined by "approximate" molecular weights. Components of such mixtures can have undesirable effects, even where one or more components have a desired effect. This publication discloses that feeding rats a diet including mixtures of (R)-3-hydroxybutyrate oligomers having an average molecular weight of 200 grams per mole elevated blood concentrations of (R)-3-hydroxybutyrate to 0.65 mM and concentrations of acetoacetate to 0.05 mM. A similar diet including (R)-3-hydroxybutyrate oligomers having a higher average molecular weight (1000 grams per mole) only elevated blood concentrations of (R)-3-hydroxybutyrate to 0.15 mM and concentrations of acetoacetate to 0.04 mM. These results indicate that the higher molecular weight oligomers disclosed in this publication do not raise the blood ketone body concentrations as effectively as lower molecular weight oligomers.

Another approach to elevating ketone body concentrations is to administer a metabolic precursor to a ketone body. One example of this approach is disclosed by Veech in published PCT Patent Application No. US99/21015. This publication discloses a cyclic trimer of (R)-3-hydroxybutyrate (triolide) as a metabolic precursor for (R)-3-hydroxybutyrate. However, the triolide is not efficiently hydrolyzed by gastric enzymes and thus is only poorly absorbed, which limits its usefulness as a (R)-3-hydroxybutyrate precursor. Additional drawbacks are associated with other proposed metabolic precursors to ketone bodies. For example, U.S. Pat. No. 6,380,244 to Martin et al. (the '244 patent), discusses the use of racemic 1,3-butanediol as a metabolic precursor to racemic 3-hydroxybutyrate. The '244 patent teaches, at column 2, line 58, that "the diol is unsuitable for use as an intravenous nutrient." Moreover, the inactive component of racemic mixtures can cause harmful side effects. For example, non-physiological isomers, such as (S)-3-hydroxybutyrate can act as competitive inhibitors to ketone body transport. Ketone body transport across the blood-brain barrier is a limiting factor to ketone body metabolism in the brain (Hawkins, R. A. et al. In Cerebral Metabolism and Neural Function; Passoneau, J. V., Hawkins, R. A., Lust, W. D., Welsh, F. A., Eds.; Williams & Wilkins, Baltimore, 1980, pp. 255-263), and thus contamination with non-physiological isomers should be avoided.

SUMMARY

Disclosed herein are novel (R)-3-hydroxybutyrate derivatives and compositions that include these derivatives. The disclosed compounds serve as precursors to ketone bodies, such as acetoacetate and (R)-3-hydroxybutyrate, and thus yield elevated blood concentrations of ketone bodies when administered to a subject.

Examples of (R)-3-hydroxybutyrate derivatives include esters of (R)-3-hydroxybutyrate and oligomers of (R)-3-hydroxybutyrate. Disclosed ester compounds include esters derived from alcohols, such as altrose, arabinose, dextrose, erythrose, fructose, galactose, glucose, glycerol, gulose, idose, lactose, lyxose, mannose, ribitol, ribose, ribulose, sucrose, talose, threose, xylitol, xylose, galactosamine, glucosamine, mannosamine, N-acetylglucosamine, mannitol, sorbitol, threitol, (S)-1,2-propanediol and (R)-1,3-butanediol. The structures of (R)-3-hydroxybutyric acid and an exemplary ester thereof (a glycerol monoester) are illustrated in FIG. 1.

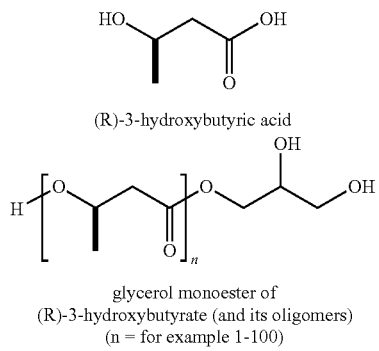

(R)-3-hydroxybutyric acid glycerol monoester of
(R)-3-hydroxybutyrate (and its oligomers)
(n = for example 1-100)

Novel methods for making (R)-3-hydroxybutyrate derivatives, particularly esters of (R)-3-hydroxybutyrate and its oligomers, such as the glycerol monoester illustrated above, are disclosed herein. Exemplary methods employ enzyme catalyzed reactions. For example, one method uses polyhydroxybutyrate depolymerase to prepare (R)-3-hydroxybutyrate derivatives. Another enzymatic reaction includes lipase catalyzed esterification in supercritical carbon dioxide. Lipase catalyzed esterification can enable selective reactions, regioselective and stereoselective esterification. The use of supercritical carbon dioxide overcomes disadvantages associated with prior methods for making (R)-3-hydroxybutyrate derivatives by substituting environmentally and physiologically benign carbon dioxide for hazardous organic solvents.

Additional exemplary methods include a method for preparing (R)-3-hydroxybutyrate and oligomers thereof from poly-(R)-3-hydroxybutyric acid. In one aspect of the method, the poly-(R)-3-hydroxybutyric acid undergoes acid-catalyzed depolymerization. Typically, the depolymerization reaction is accomplished in supercritical carbon dioxide.

In another embodiment (R)-3-hydroxybutyrate and oligomers thereof are produced via enzymatic depolymerization of poly-(R)-3-hydroxybutyric acid. In certain aspects of this embodiment, a depolymerase is used in supercritical carbon dioxide to produce a desired (R)-3-hydroxybutyrate-containing product.

The disclosed (R)-3-hydroxybutyrate derivatives can be administered to provide and maintain a blood ketone body concentration sufficient to overcome or ameliorate metabolic disorders, such as insulin deficiencies or resistance. Moreover, because the disclosed (R)-3-hydroxybutyrate derivatives can be used to increase metabolic efficiency, they can be administered orally as a nutritional or dietary supplement to improve physical performance. Indeed, because the disclosed (R)-3-hydroxybutyrate derivatives can provide a substantial portion of a subject's caloric intake, the derivatives are advantageously formulated in a food or drink. Alternatively, the compositions can be administered parenterally.

BRIEF DESCRIPTION OF THE DRAWINGS

FIG. 1 is a graph of blood ketone body concentration versus time in rats fed 1.8 grams of a (R)-3-hydroxybutyrate derivative per kilogram of body weight.

DETAILED DESCRIPTION

The disclosure describes compositions for inducing ketosis by elevating ketone body concentrations in blood. The present compositions can be used therapeutically to treat several diseases and also can be used as nutritional supplements to increase metabolic efficiency.

I. TERMS

The following explanations of terms and methods are provided to better describe the present disclosure and to guide those of ordinary skill in the art in the practice of the present disclosure.

"Derivative" refers to a compound or portion of a compound that is derived from or is theoretically derivable from a parent compound.

The term "hydroxyl group" is represented by the formula —OH.

The term "alkoxy group" is represented by the formula —OR, where R can be an alkyl group, including a lower alkyl group, optionally substituted with an alkenyl, alkynyl, aryl, aralkyl, cycloalkyl, halogenated alkyl, or heterocycloalkyl group, as defined below.

The term "ester" is represented by the formula —OC(O) R, where R can be an alkyl, alkenyl, alkynyl, aryl, aralkyl, cycloalkyl, halogenated alkyl, or heterocycloalkyl group, as defined below.

The term "alkyl group" is defined as a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms.

The term "alkenyl group" is defined as a hydrocarbon group of 2 to 24 carbon atoms and structural formula containing at least one carbon-carbon double bond.

The term "alkynyl group" is defined as a hydrocarbon group of 2 to 24 carbon atoms and a structural formula containing at least one carbon-carbon triple bond.

The term "halogenated alkyl group" is defined as an alkyl group as defined above with one or more hydrogen atoms present on these groups substituted with a halogen (F, Cl, Br, I).

The term "cycloalkyl group" is defined as a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "aliphatic group" is defined as including alkyl, alkenyl, alkynyl, halogenated alkyl and cycloalkyl groups as defined above. A "lower aliphatic group" is an aliphatic group that contains from 1 to 10 carbon atoms.

The term "aryl group" is defined as any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "aralkyl" is defined as an aryl group having an alkyl group, as defined above, attached to the aryl group. An example of an aralkyl group is a benzyl group.

"Esterification" refers to the reaction of an alcohol with a carboxylic acid or a carboxylic acid derivative to give an ester.

"Transesterification" refers to the reaction of an ester with an alcohol to form a new ester compound.

"Treating" a disease or disorder refers to a therapeutic intervention that ameliorates a sign or symptom of a disease or pathological condition or inhibits the disease from appearing, progressing or developing fully.

The term "3-hydroxybutyrate" is used interchangeably with the term "3-hydroxybutyric acid." Unless otherwise specified it is understood The terms "β-hydroxybutyrate" or "β-hydroxybutyric acid" also may be used to refer to this compound.

II. COMPOSITIONS

The compositions can include (R)-3-hydroxybutyrate derivatives, such as oligomers of (R)-3-hydroxybutyrate. Particular compounds and compositions disclosed herein include ester derivatives of (R)-3-hydroxybutyrate oligomers. For example, one particular such ester derivative disclosed herein has Formula 1. Formula can be produced by esterifying the polyhydric alcohol glycerol with two (R)-3-hydroxybutyrate trimers.

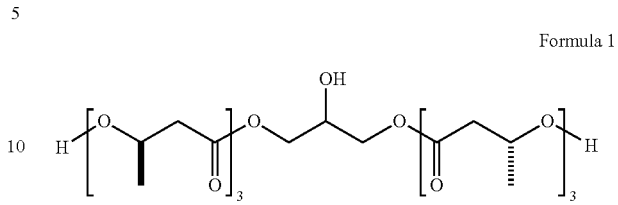

Formula 1

More generally, particular compounds disclosed herein have structures according to Formula 2. Scheme 1 also illustrates that such compounds typically are produced by esterification.

SCHEME 1

Formula 2

With reference to Scheme 1 and Formula 2, n can be any integer, and typically is an integer from 1 to about 100. More typically n is an integer from 1 to about 10. One advantage of the compositions disclosed herein is that they include compounds having defined structures. For example, the compounds disclosed herein, such as compounds according to Formula 2, can be prepared such that the compounds in a given composition have the same number of (R)-3-hydroxybutyrate derivatives (n); such compounds are termed "defined" compounds.

With reference to Formula 2, R can be any alkyl group that, with the ester oxygen atom, constitutes a physiologically compatible alkoxy group upon ester hydrolysis. The term "physiologically compatible" refers to alcohols that are substantially non-toxic when released in vivo via esterase or ester cleavage reactions. Certain alcohols are physiologically compatible at low concentration, but can provoke undesired reactions if present at high concentration. For example, ethanol is physiologically compatible at low concentrations but not at high concentrations. Thus ethyl ester (R)-3-hydroxybutyrate derivatives are useful at the lower dosages disclosed herein, but may have undesired effects at the higher dosages.

Physiologically compatible alcohols suitable for forming esters with (R)-3-hydroxybutyrate and derivatives thereof include monohydric and polyhydric alcohols. Esters of polyhydric alcohols deliver a higher density of (R)-3-hydroxybutyrate equivalents per equivalent of (R)-3-hydroxybutyrate derivative using shorter (R)-3-hydroxybutyrate oligomers. Shorter oligomers generally are more readily hydrolyzed to give elevated concentrations of (R)-3-hydroxybutyrate in blood. Examples of polyhydric alcohols suitable for preparing such esters include carbohydrates and carbohydrate derivatives, such as carbohydrate alcohols, examples of carbohydrates include, without limitation, altrose, arabinose, dextrose, erythrose, fructose, galactose, glucose, gulose, idose, lactose, lyxose, mannose, ribose, sucrose, talose, threose, xylose and the like. Additional examples of carbohydrates useful for preparing (R)-3-hydroxybutyrate derivatives include amino derivatives, such as galactosamine, glucosamine and mannosamine, including N-acetyl derivatives, such as N-acetylglucosamine and the like. Examples of carbohydrates also include carbohydrate derivatives, such as alkyl glycosides. Examples of carbohydrate alcohols include, without limitation, glycerol, mannitol, ribitol, sorbitol, threitol, xylitol and the like. The enantiomers of the above-listed carbohydrates and carbohydrate alcohols also can be used to prepare (R)-3-hydroxybutyrate derivatives according to Formula 2.

Formula 3, represents (R)-3-hydroxybutyrate and its oligomers esterified with monohydric or polyhydric alcohols to yield novel (R)-3-hydroxybutyrate derivatives.

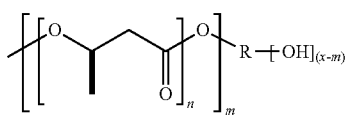

Formula 3

Polyhydric alcohols can be acylated at one or more hydroxyl groups to produce compounds according to Formula 3. For example, with reference to Formula 3, x represents the number of hydroxyl groups present on the polyhydric alcohol (prior to esterification), m represents the number of (R)-3-hydroxybutyrate oligomers attached to R via ester bonds and n represents the number of (R)-3-hydroxybutyrate residues per oligomer. Thus, x-m equals the number of hydroxyl groups remaining, if any, following esterification. For example if R is an alcohol that has 5 hydroxyl groups and three are esterified with (R)-3-hydroxybutyrate (making n equal to 1), x is 5, m is 3 and x-m equals 2. The compound of Formula 1 is another specific example of a compound described by Formula 3, wherein n is 3, m is 2 and x is 3.

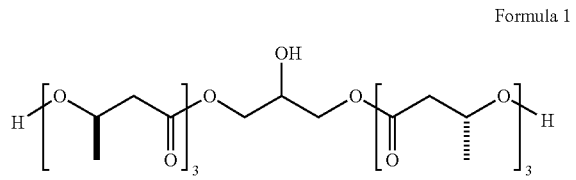

Formula 1

With continued reference to Formula 3, R can be derived from a polyhydric alcohol containing any number (x) of hydroxyl groups, although typically x is less than about 100. R can be derived, for example from a polysaccharide group. Such groups typically have from about 8 to about 20 hydroxyl groups. In several embodiments R is a monosaccharide having 4 or 5 hydroxyl groups. Thus in these embodiments R can have from 1 to 5 (R)-3-hydroxybutyrate groups or (R)-3-hydroxybutyrate oligomers appended via ester bonds. In other embodiments R contains more than 5 hydroxyls, for example when R is an oligosaccharide derivative. In exemplary embodiments R is a diol (x equal to 2), such as 1,2-propanediol or a triol (x equal to 3), such as 1,3-butanediol, glycerol or threitol.

With continued reference to Formula 3, m can be any integer that is less than or equal to x. Thus, m typically is an integer from 1 to about 100, and more typically m ranges from 2 to about 20. Particular examples of disclosed compounds have m values from 1 to about 8. Similarly, n can be any integer, and typically is an integer from 1 to about 100. More typically n is an integer from 1 to about 20. In particular compounds n is between 1 and 10.

Exemplary disclosed compounds according to Formula 3 are described in Table 1, below.

TABLE 1

| Alcohol/number of hydroxyls (x) | (R)-3-hydroxybutyrate residues (n) | ester bonds (m) |
|---|---|---|
| (R)1,3-butanediol/2 | 3 | 1 |
| (R)1,3-butanediol/2 | 3 | 2 |
| glycerol/3 | 3 | 2 |
| glycerol/3 | 3 | 3 |
| glucose/5 | 1 | 5 |
| galactose/5 | 5 | 1 |
| galactose/5 | 3 | 4 |
| mannitol/6 | 2 | 6 |
| sucrose/7 | 1 | 7 |
| sucrose/7 | 3 | 7 |
| sucrose/7 | 6 | 1 |

In Formula 3 and Table 1, each (R)-3-hydroxybutyrate oligomer is identified has containing the same number of (R)-3-hydroxybutyrate residues, however this is not/necessary. For example, a polyhydric alcohol can be esterified with two or more (R)-3-hydroxybutyrate oligomers containing different numbers of (R)-3-hydroxybutyrate residues. Some examples of such compounds have Formula 4, wherein m and n are not equal.

With continued reference to Formula 4, the polyhydric alcohol used to prepare (R)-3-hydroxybutyrate derivatives according to this Formula is (R)-1,3-butanediol. This diol can be selectively acylated with (R)-3-hydroxybutyrate and oligomers thereof at one or both hydroxyl groups. Thus, exemplary embodiments include compounds according to Formulas 4 and 5, shown below. As noted above, n and m can be the same or different and have the numerical values set forth with respect to Formula 3.

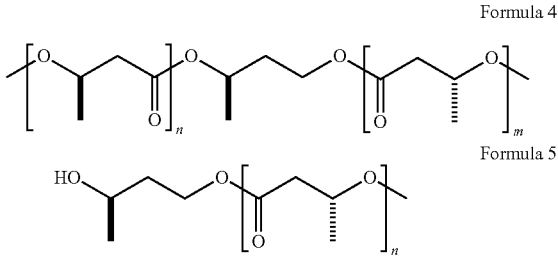

Formula 4

Formula 5

Because (R)-3-hydroxybutyrate derivatives according to Formulas 4 and 5 release (R)-1,3-butanediol in vivo, which is oxidized to (R)-3-hydroxybutyrate and acetoacetate in the liver, (R)-1,3-butanediol is a particularly useful physiologically compatible alcohol for preparing (R)-3-hydroxybutyrate derivatives.

Providing ketone bodies as (R)-3-hydroxybutyrate esters offers several advantages over prior known compositions. For example, the present esters are not contaminated with significant amounts of a non-physiological stereoisomer. Thus, the present compounds do not provoke undesired side effects or suffer from competitive inhibition by the non-physiological stereoisomer.

In one embodiment, the compositions include mixtures of (R)-3-hydroxybutyrate derivatives. For example, two or more (R)-3-hydroxybutyrate ester derivatives according to Formulas 2, 3 or 4 can be formulated and administered in the same composition. Typically these different derivatives have different R groups, so that potential undesired side effects of alcohol release in vivo are mitigated. Such (R)-3-hydroxybutyrate derivatives including different R groups can be administered in any useful proportion. For example, when two different (R)-3-hydroxybutyrate derivatives are administered, they can be administered in equal amounts or in different amounts, such as in a ratios of from about 2:1 to about 10:1. By way of example, other useful ratios include 2:1, 3:1 and 4:1 proportions of different (R)-3-hydroxybutyrate derivatives.

Similarly, different (R)-3-hydroxybutyrate derivatives having different oligomeric (R)-3-hydroxybutyrate groups can be formulated in the same composition. Such formulations are useful for tailoring the release rate of (R)-3-hydroxybutyrate because oligomers having different lengths tend to exhibit different release rates, with longer oligomers generally exhibiting slower release rates.

Compositions disclosed herein typically are nontoxic, sterile and pyrogen free, particularly endotoxin free. Compositions can be assessed for purity by determining their physical properties as is known to those of ordinary skill in the art. For example, color, pH, sterility, endotoxin presence, toxicity and stability can be assayed. High performance liquid chromatography (HPLC), mass spectrometry and NMR, particularly proton NMR, are particularly useful techniques for assessing purity. The compositions can be formulated in a palatable form for administration as a food additive or supplement. Such palatable forms are typically odor free or are masked or coated as is known to those of ordinary skill in the art of pharmaceutical formulation. Pharmaceutical formulations can include additional components, such as carriers. The pharmaceutically acceptable carriers useful for these formulations are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Where the disclosed compounds are administered orally, particularly when they are administered as a nutritional supplement, the compounds can be mixed with a foodstuff base. Such mixtures can be in the form of an emulsion or an admixture with solid food. For example, health bars, without limitation, can be prepared by combining various excipients, such as binders, fillers, flavorings, colorants and the like, along with one or more (R)-3-hydroxybutyrate derivatives, and mixing to a plastic mass consistency. The mass is then either extruded or molded to form "candy bar" shapes that are then dried or allowed to solidify to form the final product.

Alternatively, the compounds can be administered orally in a liquid dosage form as a solution, emulsion or suspension. The liquid dosage form can contain, for example, suitable solvents, preservatives, emulsifying agents, suspending agents, diluents, sweeteners, melting agents, and coloring and flavoring agents, which are known to those of ordinary skill in the art. The compounds also can be added to liquid vitamin formulations and electrolyte containing drinks. Drinks may be in the form of energy drinks, sports drinks, fruit drinks, citrus drinks, carbonated drinks, dry drink mixes, other suitable drink mediums or combinations thereof.

To maintain elevated blood ketone body concentrations over a 24 hour period, delayed release formulations can be used. The release of the (R)-3-hydroxybutyrate derivatives can be controlled by a number of formulation techniques. For example, techniques such as enteric coatings, film coatings, microencapsulation and the like can be used to retard release of the (R)-3-hydroxybutyrate derivatives as is known to those of ordinary skill in the art.

III. METHODS FOR PREPARING (R)-3-HYDROXYBUTYRATE DERIVATIVES

The disclosed (R)-3-hydroxybutyrate derivatives can be produced using chemical techniques, enzymatic techniques, transgenic organisms, or combinations thereof. In one embodiment, polymers of (R)-3-hydroxybutyrate (poly-(R)-3-hydroxybutyric acid), such as naturally occurring polymers, which are commercially available from, for example, Aldrich, Milwaukee, Wis., are converted to the thermodynamically favored cyclic trimer (triolide) by the method of Seebach and coworkers. See, Seebach et al., *Eur. J. Biochem.* 1994, 224, 317-328; *Helv. Claim. Acta* 1982, 65, 495-503; *Angew. Chem. Int. Ed. Engl.* 1992, 31, 434, 435, all of which are incorporated herein by reference.

The triolide is a versatile intermediate that can be converted to several different (R)-3-hydroxybutyrate derivatives. Exemplary ester derivatives, such as those according to Formula 2 and 3, can be produced from the triolide by chemical and/or chemoenzymatic methods. In one example of a chemoenzymatic method, the triolide is treated with a lipase in the presence of (R)-1,3-butanediol to afford the novel ester product shown in Scheme 2, below.

SCHEME 2

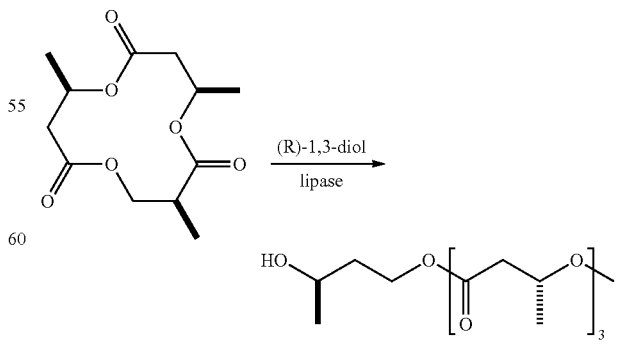

Additional methods for making (R)-3-hydroxybutyrate derivatives include esterifying or transesterifying linear oligomers of (R)-3-hydroxybutyrate and transesterifying cyclic (R)-3-hydroxybutyrate oligomers containing four or more (R)-3-hydroxybutyrate residues. For example, (R)-3-hydroxybutyrate oligomers having defined length can be produced by enzymatic depolymerization of poly-(R)-3-hydroxybutyric acid. Specifically, Wang et al. (*Biomacromolecules* 2002, 3, 838-834, this publication is incorporated herein by reference) have reported conditions for producing the (R)-3-hydroxybutyrate dimer via depolymerization. The (R)-3-hydroxybutyrate dimer can be esterified with an alcohol to yield, for example, compounds according to Formula 6.

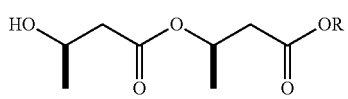

Formula 6

In one embodiment, polymers of (R)-3-hydroxybutyrate (poly-(R)-3-hydroxybutyric acid), are converted to (R)-3-hydroxybutyrate and/or oligomers thereof via acid catalyzed depolymerization. In one aspect, the depolymerization is performed in supercritical carbon dioxide that includes water as a cosolvent. The pH of water in contact with supercritical carbon dioxide is approximately 2.9 due to the formation of carbonic acid, which can accelerate the depolymerization reaction (Toews, et al. *Anal. Chem.* 1995, 67, 4040). Optionally, an acid catalyst can be added to the supercritical carbon dioxide to promote the depolymerization reaction. Suitable acid catalysts are known to those of ordinary skill in the art and include, for example, organic acids, such as 4-toluenesulfonic acid.

In another example of acid catalyzed depolymerization, a Lewis acid is used to promote the depolymerization reaction. For example, Seebach et al. *Helv. Chim. Acta* 1982, 65, 495-503, disclose a titanium catalyzed transesterification protocol for producing ethyl (R)-3-hydroxybutyrate from poly-(R)-3-hydroxybutyric acid.

Another chemical process for producing oligomers of (R)-3-hydroxybutyrate from poly-(R)-3-hydroxybutyric acid proceeds via direct hydrogenation of the polymer. For example, poly-(R)-3-hydroxybutyric acid is contacted with a hydrogenation catalyst, such as a noble metal catalyst, or a chromite catalyst, such as copper chromite, in the presence hydrogen at elevated pressure. This process can be performed in supercritical carbon dioxide. Use of supercritical carbon dioxide yields several advantages over conventional solvents. Specifically, toxic solvent residue is not introduced into the disclosed compositions and costly solvent disposal and clean-up costs are avoided. These advantages are particularly relevant to the presently disclosed therapeutic agents.

In another embodiment, (R)-3-hydroxybutyrate is prepared from ethyl acetoacetate, which is readily available from various commercial sources. For example, as is known to those of ordinary skill in the art, ethyl acetoacetate can be reduced stereospecifically using chemical or enzymatic techniques to give the desired (R)-3-hydroxybutyrate product. Similarly, ethyl acetoacetate can be reduced at the carboxylate carbon either before or after the stereospecific reduction to afford (R)-1,3-butanediol. Beta keto esters, such as ethyl acetoacetate, can be stereospecifically reduced both enzymatically, using for example a dehydrogenase, and chemically using various catalysts as is well known to those of ordinary skill in the art. For example, Brown et al. *J. Org.* *Chem.* 1989, 54, 1577-1583; *J. Org. Chem.* 1989, 54, 4501-1511, describe the stereospecific reduction of such beta keto ester compounds using alkyl borane complexes. Additional suitable methods that employ catalytic ruthenium complexes have been reviewed by Everaere et al. *Adv. Synth. Catal.* 2003, 345, 67-77. The Brown and Everaere publications are incorporated herein by reference. A catalytic system for enzymatically preparing (R)-3-hydroxybutyrate from ethyl acetoacetate described in the examples section below.

In one embodiment, polymers of (R)-3-hydroxybutyrate are converted to useful (R)-3-hydroxybutyrate oligomers and derivatives thereof by using enzymatic catalysis. These enzymatic methods also can be used to produce intermediates of useful (R)-3-hydroxybutyrate-containing compounds. For example, numerous polyhydroxyalkanoate depolymerase enzymes are produced in various bacteria and can be expressed as is known to those of ordinary skill in the art. For a review, see Jendrossek, D. *Extracellular PHA Depolymerases—the Key Enzyme of PHA Degradation*. In: Biopolymers. Part 3b, Polyesters, (Steinbüchel and Doi Eds.) pp. 41-83. Wiley-VCH, Weinheim, The Jendrossek review is incorporated herein by reference. Useful depolymerase enzymes include the family PhaZ1-PhaZ7, from the subgroup EC 3.1.1.75, which are produced by the polyhydroxyalkanoate-degrading bacterium *Paucimonas lemoignei* can be used to convert poly-(R)-3-hydroxybutyric acid to (R)-3-hydroxybutyrate and oligomers thereof. PhaZ5, for example can be produced via expression in *Bacillus subtilis*, as described by Braaz et al. *FEMS Microbiol. Lett.* 2002, 209, 237-241, which is incorporated herein by reference. Similarly, PhaZ7 can be produced from *Paucimonas lemoignei* as described by Handrick et al. *J. Biol. Chem.* 2001, 276, 36215-36224 and Braaz et al. *FEMS Microbiol. Lett.* 2003, 224, 107-112, and used to produce useful oligomeric (R)-3-hydroxybutyrate derivatives. Both of these publications are incorporated herein by reference. The depolymerase and conditions for depolymerization can be selected by those of ordinary skill in the art based upon the product or mixture of products desired. For example, in certain embodiments disclosed herein it is desirable to produce oligomers of (R)-3-hydroxybutyrate, such as dimers, trimers, tetramers, pentamers, and the like, while minimizing the presence of (R)-3-hydroxybutyrate monomer. PhaZ7, for example, favors the (R)-3-hydroxybutyrate pentamer. In certain other embodiments (R)-3-hydroxybutyrate monomer is the desired product. Oligomers and ester derivatives thereof containing seven or fewer (R)-3-hydroxybutyrate units have been demonstrated to yield particularly desirable blood ketone body concentrations upon oral administration. However (R)-3-hydroxybutyrate octamers and higher oligomers and derivatives thereof also are useful as therapeutics and nutritional supplements.

Methods for preparing higher oligomers of (R)-3-hydroxybutyrate can employ enzymatic depolymerization techniques, as discussed above, or can use conventional synthetic chemistry techniques. For example, oligomeric (R)-3-hydroxybutyrate can be prepared by iterative esterification of (R)-3-hydroxybutyrate according to the method taught by U.S. Pat. No. 5,625,030 to Williams et al. (Williams), which is incorporated herein by reference. Such oligomeric (R)-3-hydroxybutyrate compounds can be esterified with a physiologically compatible alcohol by the methods disclosed by Williams, and those reviewed in Haslam, E. *Tetrahedron* 1980, 36, 2409-2434, which is incorporated herein by reference. Thus, (R)-3-hydroxybutyrate oligomers having any length can be prepared and used to produce the therapeutic (R)-3-hydroxybutyrate derivatives disclosed herein.

In one example a (R)-3-hydroxybutyrate oligomer is prepared as shown in Scheme 2, below. With reference to Scheme 2, the (R)-3-t-butyldimethylsilyloxybutyrate derivative can be prepared under the conditions disclosed by Greene and Wuts in *Protective Groups in Organic Synthesis*, 3$^{rd}$ ed.; Wiley-Interscience, New York, (1999), which is incorporated herein by reference. Step one in Scheme 2 is attaching the protected (R)-3-hydroxybutyrate derivative to a solid support as taught by Barlos and coworkers (Barlos et al. *Tetrahedron Lett.* 1989, 30, 3947; ibid. 3943, both of which are incorporated herein by reference). Step 2 is selective deprotection of the solid support-bound (R)-3-hydroxybutyrate derivative. Suitable conditions for this reaction include using fluoride sources as taught by Greene and Wuts, an exemplary reagent for this reaction is TAS-F, which is commercially available from Aldrich, Milwaukee, Wis. (See, Roush et al. *J. Org. Chem.* 1998, 63, 6436, which is incorporated herein by reference). Other suitable reagents for accomplishing step 2 in Scheme 2, including other fluoride sources, are well-known to those of ordinary skill in the art of synthetic chemistry. With reference to step 3, a second (R)-3-hydroxybutyrate derivative is introduced by a condensation reaction. Suitable conditions for this condensation include using a carbodiimide reagent, such as diisopropylcarbodiimide (DIC) or dicyclohexylcarbodiimide, optionally in combination with a catalytic amount of dimethylaminopyridine (DMAP). Additional suitable reaction conditions for step 3 are disclosed in the Williams patent. Optionally, steps 2 and 3 can be repeated any number of times to provide (R)-3-hydroxybutyrate oligomers of a desired length. Step 4, cleavage, involves treatment of the solid support-bound (R)-3-hydroxybutyrate derivative with an acid, typically a weak acid, such as acetic acid. Specific conditions involve treating the solid support with an acetic acid, trifluoroethanol, dichloromethane mixture (2:2:6 ratio) for approximately two hours at room temperature.

Scheme 3

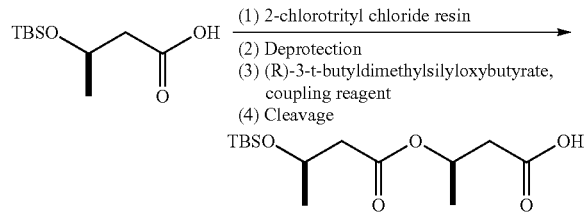

One or more equivalents of the product provided in Scheme 2 can be esterified with a physiologically compatible alcohol. For example, if the alcohol is a polyhydric alcohol, the stoichiometry of the reaction can be chosen so that each hydroxy group of the alcohol is esterified with the dimeric (R)-3-hydroxybutyrate derivative. Esterification of the defined oligomeric (R)-3-hydroxybutyrate derivatives produced as described herein can be esterified as taught by the '339 publication. Moreover, numerous suitable esterification conditions are disclosed by the Williams patent, and other conditions are well known to those of ordinary skill in the art. Removal of the silyl group from the resulting ester compound using conditions disclosed by Greene and Wuts, affords the desired (R)-3-hydroxybutyrate derivative.

Another chemical method for preparing oligomers containing two or more (R)-3-hydroxybutyrate residues uses (R)-3-hydroxybutyrate as a starting material. For example, Seebach and coworkers describe using the corresponding acid chloride derivative of 3-hydroxybutyrate to assemble 3-hydroxybutyrate oligomers in solution (Seebach et al. *Helv. Chim. Acta* 1988, 71, 155-167, which is incorporated herein by reference). Acid chlorides also can be formed from 3-hydroxybutyrate oligomers. For example, the acid chloride of the dimeric compound prepared according to Scheme 2, above, can be prepared according to the method of Seebach et al. The corresponding acid chloride can be reacted with physiologically compatible alcohols to afford, after deprotection, exemplary novel (R)-3-hydroxybutyrate derivatives.

The various alcohols for preparing (R)-3-hydroxybutyrate derivatives can be produced by any method that affords the desired physiologically compatible alcohol. An exemplary alcohol, (R)-1,3-butanediol, can be produced from (R)-3-hydroxybutyrate via reduction of the carboxylic acid moiety. Reagents and methods for reducing the carboxylic acid group are found in R. C. Larock, Comprehensive Organic Transformations, VCH publishers, 1989, pp. 432-434, which is incorporated herein by reference. This route is particularly convenient because (R)-3-hydroxybutyrate is readily available as a single enantiomer from several sources. For example, (R)-3-hydroxybutyrate can be produced via enzymatic depolymerization of its naturally occurring polymer. For exemplary methods, see Shang et al. *Appli. Environ. Microbiol.* 1994, 60, 1198-1205, and U.S. Pat. No. 6,472, 188 to Lee et al., both of which are incorporated herein by reference. The poly-(R)-3-hydroxybutyric acid starting material for the depolymerization methods can be produced by any of several methods, examples of which are taught in U.S. Pat. No. 5,569,595 to Dennis and U.S. Pat. No. 6,492, 134 to Aquin.

In another example, lipase catalyzed esterification of (R)-1,3-butanediol with the triolide compound yields the novel bis-esterified diol according to Scheme 3, below. The reaction pathways of Scheme 1 and Scheme 3 can be selected by using different lipase enzymes and/or varying reaction conditions, such as reagent concentration and stoichiometry as is known to those of ordinary skill in the art.

Scheme 4

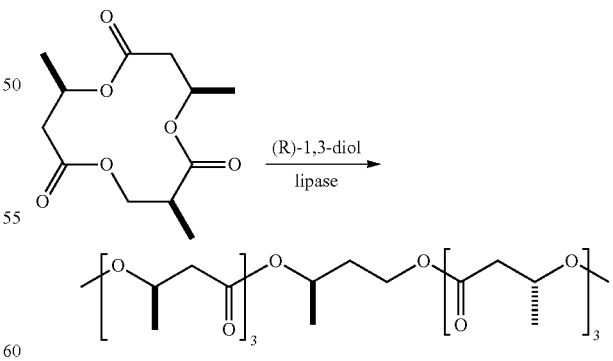

Typically lipases carry out their customary reactions, the hydrolysis of ester bonds, in aqueous solvents. However in organic solvents, where water is substantially excluded, lipases can efficiently catalyze esterification reactions. These enzymes can be used to esterify a wide variety of substrates and also can catalyze transesterification reactions. Unfortunately, the use of organic solvents has several drawbacks, particularly for pharmaceutical and food industry applications. For example, organic solvents are expensive and often flammable. Moreover many organic solvents are toxic and therefore organic solvent contamination in pharmaceutical or nutritional products can be a serious problem. Thus it is important to ensure that pharmaceutical and nutritional products are free from solvent contamination, which introduces additional complications and expense.

Prior attempts to use metabolic precursors of ketone bodies, such as (R)-3-hydroxybutyrate derivatives also have been unsuccessful in part due to the methods used to prepare such derivatives. Current methods for preparing (R)-3-hydroxybutyrate derivatives also limit the use of these compounds due to the high cost of the product and the introduction of product contamination inherent in the methods. For example, preparations of such derivatives that employ organic solvents are costly and can contaminate the product with toxic solvent residue.

One embodiment for making (R)-3-hydroxybutyrate derivatives overcomes the drawbacks of using organic solvents by using supercritical fluids, particularly supercritical carbon dioxide as a reaction medium. Supercritical fluids are by definition at a temperature and pressure greater than or equal to the critical temperature and pressure of the fluid. Carbon dioxide's critical pressure is about 7,370 kilopascals (kPa) and critical temperature is about 31 degrees Celsius (° C.), so supercritical applications using carbon dioxide typically operate at temperatures between about 32° C. and 49° C. and pressures between about 7,370 and 24,000 kPa. Supercritical solvents, particularly supercritical carbon dioxide, provide many advantages over conventional organic solvents. For example, carbon dioxide is an environmentally benign reaction medium. An exemplary method for performing enzymatic reactions in supercritical fluids is disclosed by U.S. Pat. No. 5,783,627 to Kao et al., which is incorporated herein by reference. Unlike conventional organic solvents, carbon dioxide can be allowed to simply evaporate without leaving a contaminating residue. Thus, the use of carbon dioxide simplifies both disposal and purification protocols.

In certain examples, the reaction medium can include supercritical carbon dioxide and a cosolvent. The cosolvent can include water and/or one or more organic cosolvents. Types of organic cosolvents include polar and non-polar cosolvents. Examples of polar organic cosolvents include methanol, ethanol, tetrahydrofuran, acetone and the like. Examples of suitable nonpolar cosolvents include hexanes, cyclohexane, toluene and the like.

Both the enzymatic and non-enzymatic methods for preparing (R)-3-hydroxybutyrate derivatives disclosed herein can be performed in supercritical carbon dioxide. However, supercritical carbon dioxide has a pH of between about 4 and about 5. This acidic pH can denature some proteins, thereby abrogating their catalytic activity. Thus, in one aspect of the method for making (R)-3-hydroxybutyrate derivatives, stabilized lipases, such as crosslinked enzyme crystal (CLEC) lipases are used. Examples of methods for making and using such stabilized lipases are disclosed in U.S. Pat. No. 5,618,710 to Navia et al. and U.S. Pat. No. 6,211,422 to DeSimone et al., both of which are incorporated herein by reference.

In another aspect, pH sensitive lipases can be used within their effective pH range by incorporating a buffer into the solvent system. Examples of buffer systems for particular pH ranges are given by Ellis and Morrison (*Methods Enzymol.* 1982, 87, 405) and by McLellan (*Anal. Biochem.* 1982, 126, 94), both of which are incorporated herein by reference. Additional suitable buffers for a given pH range are known to those of ordinary skill in the art.

Suitable lipases for preparing (R)-3-hydroxybutyrate derivatives can be selected based upon the desired derivative. For example, lipases can be screened for the ability to catalyze a desired reaction by the protocol described in Example 1, below. Suitable lipases for screening to determine the optimal catalyst are disclosed by Whitesides and Wong (1994, *Enzymes in Synthetic Organic Chemistry, Elsevier*, Oxford), Gross et al. (*Chem. Rev.* 2001, 101, 2097-2124) and Michor et al. (*Biotechnology Letters* 1996, 18, 79-84), these references are incorporated herein by reference. A source for suitable lipases is Biocatalytics, Inc., Pasadena, Calif., which sells a screening set of lipases under the trade name "Chirazyme." It is currently believed that porcine pancreatic lipase (PPL), the lipase from *P. cepacia* (lipase PC), and *Pseudomonas* sp. lipase (PSL) are particularly useful lipases for preparing (R)-3-hydroxybutyrate esters.

Immobilized lipases are useful for preparing (R)-3-hydroxybutyrate esters. Immobilized lipases provide advantages in efficiency, catalytic turnover and ease of product purification. Lipases can be immobilized on any substrate, with typical examples including glass or gold surfaces, polymer beads, silica, Celite and the like. U.S. Pat. No. 6,080,402 to Reetz et al. and U.S. Pat. No. 6,398,707 to Wu et al., which are incorporated herein by reference, describe useful lipase immobilization techniques.

In other embodiments, the (R)-3-hydroxybutyrate derivatives disclosed herein can be produced, or intermediates to the derivatives can be produced, by microorganisms. For example, in one embodiment poly-(R)-3-hydroxybutyric acid is used as a starting material for producing compounds according to Formulas 1 and 2. The genes responsible for producing poly-(R)-3-hydroxybutyric acid have been cloned and expressed, and this material can be produced in several different microorganisms under a variety of conditions. See, Rhie and Dennis, *Appl. Environ. Microbiol.* 1995, 61, 2487-2492, which is incorporated herein by reference. Poly-(R)-3-hydroxybutyric acid can be converted into the therapeutic compounds disclosed herein by chemical methods, enzymatic methods, and combinations thereof. In another embodiment, the poly-(R)-3-hydroxybutyrate derivatives are produced completely in microorganisms.

IV. METHODS FOR USING (R)-3-HYDROXYBUTYRATE DERIVATIVES

The disclosed (R)-3-hydroxybutyrate derivatives enable the treatment of several diseases that benefit from elevated levels of ketone bodies. For example a variety of neurological disorders, including epilepsy and myoclonus, and particularly neurodegenerative diseases, including, without limitation, those such as Alzheimer's disease, vascular dementia, Lewy body type senile dementia, Lafora body dementia, Parkinson's disease, mitochondrial myopathy encephalopathy lactacidosis stroke syndrome (MELAS syndrome), Pick's disease and muscular dystrophy, and their associated effects can be treated effectively with the present (R)-3-hydroxybutyrate derivatives. Because the disclosed compositions also can be used as a foodstuff to mimic the effects of a ketogenic diet, the compositions also are useful for treating obesity.

Muscular dystrophic states can be treated using the disclosed compounds and compositions. For example, Duchenne's and Becker's muscular dystrophies, Friedreich's ataxia, myoclonus epilepsy associated with ragged-red fibers (MERRF) syndrome, Kearns-Sayre syndrome, Leigh's syndrome and muscle wasting can be treated by administering (R)-3-hydroxybutyrate derivatives disclosed herein.

Many diseases, including several listed above, have secondary effects caused by damage due to excessive free radical production and can be treated using the (R)-3-hydroxybutyrate derivatives disclosed herein. For example, free radical damage has been implicated in neurological disorders, such as Parkinson's disease, amyotrophic lateral sclerosis (Lou Gehrig's disease) and Alzheimer's disease. Additional diseases in which excessive free radical damage occurs generally include hypoxic conditions and a variety of other disorders. More specifically, disorders in which excessive free radical damage is implicated include ischemia, ischemic reperfusion injury (such as coronary or cerebral reperfusion injury), myocardial ischemia or infarction, cerebrovascular accidents (such as a thromboembolic or hemorrhagic stroke) that can lead to ischemia in the brain, operative ischemia, traumatic hemorrhage (for example, a hypovolemic stroke that can lead to CNS hypoxia or anoxia), resuscitation injury, spinal cord trauma, inflammatory diseases, autoimmune disorders (such as rheumatoid arthritis or systemic lupus erythematosis), Down's syndrome, Hallervorden-Spatz disease, Huntingtons chorea, Wilson's disease, diabetic angiopathy (such as peripheral vascular disease or retinal degeneration), uveitis, chronic obstructive pulmonary disease (COPD), including chronic bronchitis and emphysema, asthma, neoplasia, Crohn's disease, inflammatory bowel disease and pancreatitis. Free radical damage is also implicated in a variety of age-related disorders, particularly ophthalmic conditions such as cataracts or age-related macular degeneration.

Thus, another advantage of the disclosed compositions is reduced free radical damage. Metabolism of the present compositions reduces free radical damage by oxidizing coenzyme-Q. The major source of mitochondrial free radicals is the semiquinone form of coenzyme-Q, which results from one electron reduction of the quinone. The semiquinone reacts directly with oxygen molecules to form the superoxide radical anion ($O_2-$). In ketone body metabolism, the concentration of the semiquinone form of coenzyme-Q is reduced. Thus, the present compositions are useful in treating free radical-associated diseases.

Metabolic efficiency is enhanced by the disclosed (R)-3-hydroxybutyrate derivatives. Thus the compounds can be administered to a subject to improve exercise efficiency and athletic performance. Moreover, conditions including, without limitation, hypoxic states, angina pectoris, coronary ischemia and organ damage secondary to coronary vessel occlusion, intermittent claudication, multi-infarct dementia, myocardial infarction, stroke, high altitude sickness and heart failure can be treated using the disclosed compounds.

The present compositions also can be used to treat conditions such as tumors, particularly brain tumors, such as astrocytoma. Indeed, metabolic control has been demonstrated to reduce angiogenesis and growth in one experimental brain tumor model (Mukherjee et al. *Br. J. Cancer* 2002, 86, 1615-1621).

Disorders of glucose metabolism, such as type I diabetes, can be treated using (R)-3-hydroxybutyrate derivatives as a source of ketone bodies. For example, disorders such as insulin resistance, including type II diabetes can be effectively treated using the compounds. Similarly, hypoglycemic and/or hypoketotic conditions resulting from metabolic disorders, such as acyl coenzyme A dehydrogenase syndrome, carnitine palmitoyl transferase deficiency types I and II (CPT-I and II), maple syrup urine disease (MSUD) or resulting from other conditions, such as pancreatic adenoma or hyperplasia, can be treated using the disclosed compounds and compositions. Additional disorders of glucose metabolism that can be treated using the disclosed (R)-3-hydroxybutyrate derivatives include, without limitation, Leprechaunism, Rabson-Mendenhall syndrome, and hypoglycemic episodes. Glut-1 deficiency, a disorder of glucose transport associated with a defect in the brain-associated glucose transport protein, also can be treated using the (R)-3-hydroxybutyrate derivatives disclosed herein.

The blood concentration of ketone bodies can be maintained at a therapeutically or nutritionally effective level by administering the appropriate amount of the (R)-3-hydroxybutyrate derivative based upon the disorder to be treated and/or the weight and energy requirements of the subject.

Using the (R)-3-hydroxybutyrate derivatives disclosed herein, desired therapeutic and nutritional effects can be sustained without resort to the ketogenic diet. During normal metabolism of these derivatives, ketone bodies, specifically, (R)-3-hydroxybutyrate and acetoacetate, are released into the blood. Typically, therapeutic blood ketone concentrations (measured as the sum of (R)-3-hydroxybutyrate and acetoacetate) range from about 0.1 to about 20 mM, more typically from about 0.2 to about 10 mM, and for some disorders, blood ketone levels of from about 2 to about 8 mM are found to be therapeutic. For example, it is currently believed that ketone body concentrations greater than about 4 mM yield a therapeutic response in refractory epilepsy (Gilbert et al., *J. Child Neurol.* 2000, 15, 787-790). However, certain disorders benefit from relatively small increases in the concentration of ketone bodies in the blood. For example, Van Hove et al. observed therapeutic effects in children afflicted with CoA dehydrogenase deficiency using oral administration of racemic sodium-3-hydroxybutyrate. The therapeutic effects were correlated with peak blood levels of 0.19 mM to 0.36 mM total concentration of (R)-3-hydroxybutyrate and acetoacetate (Van Hove et al., *Lancet* 2003, 361, 1433-1435).

The therapeutic blood ketone body concentrations observed by Van Hove et al., can be produced in a 70 kilogram man using from about 5 to about 70 grams per day of (R)-3-hydroxybutyrate equivalents. However, the blood ketone concentrations observed in a fasting man are higher, typically from about 5 mM to about 7 mM. A fasting 70 kilogram man produces about 150 grams of ketone bodies per day, thereby yielding the ketone body concentration in blood of from about 5 to about 7 mM. Thus, to achieve the concentrations of ketone bodies observed under long term fasting or the ketogenic diet, a 70 kilogram man will consume about 150 grams of (R)-3-hydroxybutyrate equivalents per day. The total amount consumed depends upon body weight and the desired effect. Typically, the weight of (R)-3-hydroxybutyrate equivalents consumed or administered per day ranges from about 5 grams to about 300 grams, and more typically from 10 grams to about 200 grams. The amount administered can be more conveniently expressed in terms of grams of (R)-3-hydroxybutyrate equivalents per day per kilogram of body weight, which typically will range from about 70 milligrams to about 5 grams per kilogram of body weight. More typically, the amount of hydroxybutyrate equivalents per day will range from about 1 gram to about 4 grams per kilogram of body weight, and most typically from about 1.5 grams to about 3 grams per kilogram of body weight.

Thus, when the disclosed (R)-3-hydroxybutyrate derivatives are used in larger amounts, they will provide a significant portion of the caloric intake of the subjects. Thus, the disclosed (R)-3-hydroxybutyrate derivatives can be administered as foodstuffs. Indeed, in one aspect, the disclosed (R)-3-hydroxybutyrate derivatives are used as a foodstuff or nutritional supplement to enhance performance.

V. EXAMPLES

The foregoing disclosure is further explained by the following non-limiting examples.

Example 1

This Example describes a protocol for determining the ability of lipases to catalyze a specific desired reaction. A grid of substrate molecules is prepared in test tubes by dissolving each substrate to a final concentration of 0.1 mM in $CH_3CN$ and mixing with 0.1 M phosphate buffer (pH 7.5). An enzyme is then added to each microtiter well and the mixture is incubated for 30 minutes. The reaction mixture in each tube is extracted three times with dichloromethane, the organic extracts are combined, dried over $MgSO_4$, and concentrated to about 0.1 mL using a nitrogen stream. The concentrated samples are then analyzed using analytical thin layer chromatography (TLC). Accordingly, each sample is spotted to a silica TLC plate (available from E. Merck, Darmstadt) and developed in a mixture of dichloromethane: methanol (99:1). The developed TLC plates are visualized using UV light and charring with a p-anisaldehyde stain (18 mL p-anisaldehyde, 7.5 mL glacial acetic acid, 25 mL concentrated $H_2SO_4$, 675 mL absolute ethanol).

Example 2

This Example describes the synthesis of the triolide of (R)-3-hydroxybutyric acid. The procedure follows the protocol of Seebach et al. *Angew. Chem. Int. Ed. Engl.* 1992, 31, 434. A mixture of poly-(R)-3-hydroxybutyric acid (50 g) and 4-toluenesulfonic acid monohydrate (21.5 g, 0.113 mole) in toluene (840 mL) and 1,2-dichloroethane (210 mL) was stirred and heated at reflux for 20 hours under a Dean-Stark trap. The resulting brown solution was cooled to room temperature and washed with a half saturated solution of sodium carbonate and with a saturated sodium chloride solution. The organic phase was dried over $MgSO_4$ and concentrated in vacuo. The resulting brown semi-solid residue was distilled using a Kugelrohr apparatus to yield a white solid (18.1 g) at 120-130° C. at 0.15 torr. Above 130° C. a waxy solid began to distill and the distillation was stopped. The distilled material had a melting point of 100-102° C. Recrystallization from hexane afforded colorless crystals (15.3 g) having a melting point of 107-108° C. $[\alpha]_D$ 35.1 (c=1.005, $CHCl_3$), (lit.=–33.9). $^1H$ NMR (300 MHz, $CDCl_3$): δ=1.30 (d, 9H, —$CH_3$); 2.4-2.6 (m, 6H; —$CH_2$—); 5.31-5.39 (M, 311; HC—O). $^{13}C$ NMR ($CDCl_3$) δ 20.86 ($CH_3$); 42.21 ($CH_2$); 68.92 (CH); 170.12 (CO). Elemental analysis: calculated for $C_{12}H_{18}O_6$: C, 55.81; H, 7.02. Found: C, 55.67; H, 7.15.

Example 3

This Example describes the preparation of (R)-1,3-butanediol from poly-(R)-3-hydroxybutyric acid via reductive depolymerization. The procedure follows the protocol of Seebach et al. *Helv. Chim. Acta* 1982, 65, 495-503. $LiAlH_4$ (10 g, 0.264 mmol) is suspended in tetrahydrofuran (460 mL) and cooled to 15° C. Poly-(R)-3-hydroxybutyric acid (30 g, 0.349 mmol) is added slowly (over 40 minutes). The mixture is then stirred at room temperature for 90 minutes and then heated to reflux for 5 hours. After stirring over night at room temperature, the mixture is cooled to 0° C. and the reaction quenched by the careful (dropwise) addition of 10 mL of water, followed by 30 mL of a 10% NaOH solution and 30 mL of water. The white precipitate formed is removed via filtration, extracted with $CH_2Cl_2$ (2×150 mL×30 minutes) removed via filtration and washed with $CH_2Cl_2$ (100 mL). The combined organic extracts were dried over $MgSO_4$ and the volatiles removed in vacuo. The residue was distilled at reduced pressure to afford 26.55 g (85%) of analytically pure (R)-1,3-butanediol.

Example 4

This Example describes the enzymatic preparation of (R)-3-hydroxybutyric acid from ethyl acetoacetate. The net reaction produces one equivalent each of (R)-3-hydroxybutyric acid and ethanol from one equivalent of ethyl acetoacetate (and water). The procedure uses two enzymes, an esterase to hydrolyze the ethyl acetoacetate to acetoacetate and ethanol and β-hydroxy butyrate dehydrogenase to stereoselectively reduce the β-keto group to form (R)-3-hydroxybutyric acid. Both enzymes are commercially available from Biocatalytics and Sigma Chemical Co.

First the formation of ethanol from ethyl acetoacetate was demonstrated as follows: An ethanol cocktail was prepared containing 2-amino-2-methylpropanol pH 9.9 (0.93 M) and NAD (3.3 mM) and 50 microliters of the ethanol cocktail were added to wells in a microplate. An esterase reaction cocktail was prepared containing imidazole pH 7 (0.1 M), $MgCl_2$ (0.005 M) and esterase isolated from pig liver (EC 3.1.1.1, 13U), and various wells received standard ethanol, esterase and/or ethyl acetoacetate to a total volume of 100 microliters. A baseline was established at 340 nm and alcohol dehydrogenase from yeast was added to initiate a reaction. The plate was then read in a kinetic mode at 340 nm. In wells containing standard ethanol and in wells containing both ethyl acetoacetate and esterase an increase in absorbance was observed indicating the production of NADH via the following scheme.

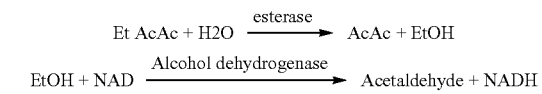

Wells containing only ethyl acetoacetate or esterase behaved the same as water blanks. This experiment indicates that neither the esterase nor the ethyl acetoacetate contain appreciable amounts of ethanol and that the esterase from pig liver effectively cleaves the ester to yield acetoacetate and ethanol.

(R)-3-Hydroxybutyric acid was prepared from ethyl acetoacetate as follows: An esterase reaction cocktail was prepared as above (imidazole pH 7 (0.1 M), $MgCl_2$ (0.005 M) and esterase isolated from pig liver (EC 3.1.1.1, 13U)). Ethyl acetoacetate (~0.1 M) was added at room temperature and the solution was placed on the lab bench. After 20 minutes 10 or 20 microliter aliquots of the lipase containing solution were transferred to a microplate containing 100 microliters of an acetoacetate cocktail containing imidazole pH 7 (0.1 M) and NADH (0.25 mM). After establishing a baseline absorbance at 340 nm, β-hydroxybutyrate dehydrogenase was added to the microplate and the plate was read in a kinetic mode. A decrease in absorbance was observed indicating a loss of NADH in the well, and evidencing the conversion of acetoacetate to (R)-3-hydroxybutyrate as described in the following reaction scheme.

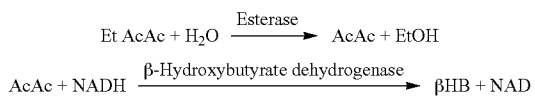

Example 5

This Example describes the preparation of ethyl (R)-3-hydroxybutyrate from ethyl acetoacetate. To wells in a microplate was added 50 microliters of a pH 7 solution containing imidazole (0.1M) and NADH (0.3 mM). Ethyl acetoacetate (3.9 mM) was added to reaction wells, water was added to control wells and a baseline was established. All wells received β-hydroxybutyrate dehydrogenase and the UV absorbance in the wells was followed kinetically. A decrease in absorbance was observed indicating the oxidation of NADH as described in the equation below:

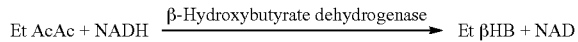

Example 6

This Example describes the oral administration of the compound produced in Scheme 3 to rats and measurement of the resulting blood ketone levels. Four Wistar rats were fasted overnight and fed 1.8 grams of the compound per kilogram by gavage feeding. 24 hours prior to gavage a cannula was inserted into the right atrium of each rat. The cannulae were used to draw blood samples for ketone body monitoring during the experiment. The results, in ketone body concentration in blood versus time after feeding, are displayed in FIG. 1. With reference to FIG. 1, increases in serum (R)-3-hydroxybutyrate and acetoacetate are observed. The peak concentration of (R)-3-hydroxybutyrate occurs at approximately 45 minutes after gavage, and the peak concentration of acetoacetate occurs at about one hour after gavage.

The invention claimed is:

1. A compound of Formula 3:

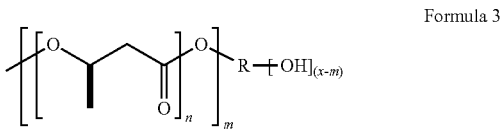

Formula 3 or a pharmaceutically acceptable salt thereof, wherein:
R is (R)-1,3-butanediol;
m is 1;
n is 1; and
x is 2.

2. A pharmaceutical composition comprising a compound of claim 1 and a pharmaceutically acceptable carrier.

3. The compound of claim 1, wherein: m is 1.

4. A pharmaceutical composition comprising the compound of claim 3 and a pharmaceutically acceptable carrier.

5. The pharmaceutical composition of claim 2, formulated for oral administration as a nutritional or dietary supplement.

6. The pharmaceutical composition of claim 4, formulated for oral administration as a nutritional or dietary supplement.

* * * * *